(12) United States Patent
Jan

(10) Patent No.: US 11,567,236 B2
(45) Date of Patent: *Jan. 31, 2023

(54) OPHTHALMIC LENS AND METHOD FOR MANUFACTURING THE SAME

(71) Applicant: BenQ Materials Corporation, Taoyuan (TW)

(72) Inventor: Fan-Dan Jan, Taoyuan (TW)

(73) Assignee: BenQ Materials Corporation, Taoyuan (TW)

( * ) Notice: Subject to any disclaimer, the term of this patent is extended or adjusted under 35 U.S.C. 154(b) by 293 days.

This patent is subject to a terminal disclaimer.

(21) Appl. No.: 16/940,531

(22) Filed: Jul. 28, 2020

(65) Prior Publication Data

US 2020/0355849 A1 Nov. 12, 2020

Related U.S. Application Data

(63) Continuation of application No. 15/679,812, filed on Aug. 17, 2017, now Pat. No. 10,782,449.

(30) Foreign Application Priority Data

Apr. 10, 2017 (TW) ................. 106111947

(51) Int. Cl.
| | | |
|---|---|---|
| *G02B 1/04* | (2006.01) | |
| *G02B 1/18* | (2015.01) | |
| *B29D 11/00* | (2006.01) | |
| *B05D 1/36* | (2006.01) | |
| *A61L 27/52* | (2006.01) | |

(52) U.S. Cl.
CPC ............. *G02B 1/043* (2013.01); *A61L 27/52* (2013.01); *B05D 1/36* (2013.01); *B29D 11/00067* (2013.01); *B29D 11/00865* (2013.01); *G02B 1/18* (2015.01)

(58) Field of Classification Search
CPC .. C09D 101/02; C09D 5/1662; C09D 5/1656; C08J 7/042; C08G 73/0672; C08G 18/755; C08G 18/672; C08G 18/61; B05D 1/36; B29D 11/00865; B29D 11/00067; A61L 2/14; A61L 2/08; A61L 2/00; A61L 27/52; G02B 1/18; G02B 1/043
USPC ................. 525/32.1, 39; 351/159.33, 159.02
See application file for complete search history.

(56) References Cited

U.S. PATENT DOCUMENTS

| | | | | |
|---|---|---|---|---|
| 2014/0163133 A1* | 6/2014 | Chan | ........................ | A61L 27/34 523/105 |
| 2014/0272013 A1* | 9/2014 | Zhao | ...................... | A23B 7/154 426/100 |
| 2014/0336040 A1* | 11/2014 | Yan | ........................ | B22F 1/0655 75/343 |
| 2015/0368408 A1* | 12/2015 | Trexler | ................... | C08B 1/003 106/163.01 |

OTHER PUBLICATIONS

Ho et al, Structure, Properties and Applications of Mussel-Inspired Polydopamine Journal of Biomedical Nanotechnology, (Year: 2014).*

* cited by examiner

*Primary Examiner* — Travis S Fissel

(57) ABSTRACT

The invention is to provide an ophthalmic lens and manufacturing method thereof. The ophthalmic lens comprises a lens body, a polydopamine layer formed on a surface of the lens body and a first cellulose nanofiber (CNF) layer bonded to the polydopamine layer.

16 Claims, No Drawings

OPHTHALMIC LENS AND METHOD FOR MANUFACTURING THE SAME

CROSS-REFERENCE TO RELATED APPLICATION

This application claims the priority benefit of Taiwanese application serial No. 106111947, filed on Apr. 10, 2017, and the priority benefit of U.S. application Ser. No. 15/679,812, filed on Aug. 17, 2017, which are incorporated herein by references.

BACKGROUND OF THE INVENTION

Field of the Invention

The present invention relates to an ophthalmic lens and a method for manufacturing the same. More particularly, the present invention relates to an ophthalmic lens with high hydrophilicity, desired optical properties and wearing comfortability, and method for manufacturing the same.

DESCRIPTION OF RELATED ART

In the early years, hard contact lens was mainly made of glass. The soft contact lens was therefore developed to improve the wearing discomfort of the hard contact lens. The soft contact lens can be classified into two categories, hydrogel contact lens and silicone hydrogel contact lens.

The main material of the hydrogel contact lens is poly-2-hydroxyethyl methacrylate (p-HEMA). Since the water content of poly-2-hydroxyethyl methacrylate (p-HEMA) is only about 38.8%, at least one hydrophilic monomer, such as, N-vinylpyrrolidone (NVP), N,N-dimethylacrylamide (DMA), methyl acrylic acid (MAA) or the like, will be added into the contact lens material to enhance the water content of the contact lens.

Contact lens requires unique safety, optical property, oxygen permeability and wearing comfortability. The hydrogel contact lens has better wearing comfortability owing to its better hydrophilicity. However, the hydrogel contact lens has lower oxygen permeability which will make the wearer suffer from corneal edema or angiogenesis when the hydrogel contact lens is worn for a long time. Several methods have been proposed in the state of the art to improve the oxygen permeability of hydrogel contact lens, such as reducing the thickness of the contact lens or enhancing the water content of the contact lens. However, the approaches mentioned above are not effective and have various disadvantages. For example, it is known that reducing the thickness of the contact lens will lower the mechanical strength of the contact lens, adding hydrophilic monomer for enhancing water content will lower the tension and toughness of the contact lens.

Comparing to the hydrogel contact lenses, the silicone hydrogel contact lens has higher oxygen permeability, therefore the development of contact lens mainly trends to silicone hydrogel contact lens in recent years. The silicone hydrogel contact lens material comprises siloxane macromer which is able to provide high oxygen permeability, thus the oxygen molecular can reach the cornea through the lens easily and result in improving the oxygen permeability of the contact lens. However, siloxane macromer is hydrophobic and has poor wetting ability, the wear's eyes will be easily dry and discomfort when wearing silicone hydrogel contact lenses It is reported that polydopamine possesses a structure similar to the adhesive proteins secreted by mussel with amounts of hydrophilic hydroxy functional groups and amine functional groups. Therefore, polydopamine has been widely used in surface modification of medical instrument for improving hydrophilicity or biocompatibility, for example, the surface of catheters, implants or tissue scaffolds made of plastic, metal, ceramic or cloth. However, because polydopamine is in dark blue, the surface modified thereby will be in brown color. Thus, the conventional method for modifying surface of medical instrument by polydopamine is not suggested to be used on articles which require for unique optical properties. In addition, because polydopamine has great absorbability for biological cell and protein, polydopamine is not highly suggested to be used in ophthalmic lens due to the deposit resistance concerns.

Therefore, an object of the present invention is to provide an ophthalmic lens having high hydrophilicity, desirable physical properties and wearing comfortability.

SUMMARY OF THE INVENTION

The present invention provides an ophthalmic lens and a method for manufacturing ophthalmic lens which has high hydrophilicity, desirable physical properties and wearing comfortability. The present ophthalmic lens comprises a polydopamine layer formed on a surface of the ophthalmic lens and a first cellulose nanofiber (CNF) layer bonded to the polydopamine layer by crosslinking agent. The hydrophobic surface of ophthalmic lens can be improved by using the cellulose nanofiber which has great hydrophilicity. Moreover, besides adhering cellulose nanofiber, the polydopamine provides a great biocompatibility and hydrophilicity, the wearing comfortability and hydrophilicity of the present ophthalmic lens can be enhanced therefore. Additionally, although the ophthalmic lens of the present invention comprises polydopamine and cellulose nanofiber, necessary physical properties of the ophthalmic lens, such as the transmittance, can still be retained.

According to an aspect of the present invention, an ophthalmic lens is provided. The present ophthalmic lens comprises a lens body, a polydopamine layer and a first cellulose nanofiber (CNF) layer. The polydopamine layer is adhered to the surface of the lens body and the first cellulose nanofiber (CNF) layer is bonded to the polydopamine layer.

In a preferred embodiment of the present invention, wherein the lens body is made of a hydrogel or a silicon hydrogel.

In a preferred embodiment of the present invention, the present ophthalmic lens further comprises a second cellulose nanofiber (CNF) layer bonded to the first cellulose nanofiber (CNF) layer.

According to another aspect of the present invention, an ophthalmic lens is provided. The present ophthalmic lens comprises a lens body, a polydopamine layer, a first cellulose nanofiber (CNF) layer and a functional layer.

In a preferred embodiment of the present invention, wherein the functional layer is selected from one of the group consisting of a second cellulose nanofiber, a zwitterionic polymer, a zwitterionic copolymer and a reactive dye or a combination thereof.

According to further another aspect of the present invention, a method for manufacturing an ophthalmic lens is provided. The method for manufacturing the ophthalmic lens comprises steps of:(a) providing a lens body, and immersing the lens body in a polydopamine solution to coat a polydopamine layer on a surface of the lens body; (b)

washing the polydopamine-coated lens body; and (c) immersing the polydopamine-coated lens body in a solution containing a first cellulose nanofiber and a crosslinking agent to form a first cellulose nanofiber layer bonded to the polydopamine layer.

In a preferred embodiment of the method of the present invention, wherein the polydopamine solution is heated at the temperature in the range of 40° C. to 80° C., and preferably in the range of 40° C. to 60° C. in the step of (a).

In a preferred embodiment of the method of the present invention, wherein the lens body is immersed in the polydopamine solution for a time in the range of 5 minutes to 30 minutes, and preferably in the range of 10 minutes to 20 minutes in the step of (a).

In a preferred embodiment of the method of the present invention, wherein the concentration of the polydopamine solution is in the range of 50 ppm to 400 ppm, and preferably in the range of 100 ppm to 300 ppm.

The method for manufacturing the ophthalmic lens can further comprise a step of preparing the polydopamine solution from dopamine in alkaline environments before the step of (a).

In a preferred embodiment of the method of the present invention, wherein the solution containing the first cellulose nanofiber and the crosslinking agent is heated at the temperature in the range of 60° C. to 121° C., and preferably in the range of 60° C. to 80° C. in the step of (c).

In a preferred embodiment of the method of the present invention, wherein the polydopamine-coated lens body is immersed in the solution containing the first cellulose nanofiber and the crosslinking agent for a time in the range of 20 minutes to 90 minutes, and preferably in the range of 30 minutes to 60 minutes in the step of (c).

In a preferred embodiment of the method of the present invention, wherein the concentration of the first cellulose nanofiber is in the range of 300 ppm to 1500 ppm, and preferably in the range of 500 ppm to 1000 ppm.

In a preferred embodiment of the method of the present invention, wherein the crosslinking agent is selected from one of the group consisting of 1,4-butanediol diglycidyl ether (BDDE), polyethylene glycol diacrylate (PEGDA), ethylene glycol diglycidyl ether, 1,6-hexanediol diglycidyl ether, polypropylene glycol diglycidyl ether, polytetramethylene glycol diglycidyl ether, neopentyl glycol diglycidyl ether, polyglycerol polyglycidyl ether, diglycerolpolyglycidyl ether, glycerol polyglycidyl ether, tri-methylolpropanepolyglycidyl ether, pentaerythritolpolyglycidyl ether, sorbitol polyglycidyl ether, 1,2,7,8-diepoxyoctane, 1,3-butadiene diepoxide, polyamidoamineepichlorohydrin and copolymer of dimethylamine and epichlorohydrin or a combination thereof.

In a preferred embodiment of the method of the present invention, wherein the concentration of the crosslinking agent is in the range of 100 ppm to 600 ppm, and preferably in the range of 200 ppm to 500 ppm.

The method for manufacturing the ophthalmic lens of the present invention can further comprises a step of (d) immersing the lens body having first cellulose nanofiber layer in a solution containing a second cellulose nanofiber for bonding a second cellulose nanofiber layer to the first cellulose nanofiber layer.

In a preferred embodiment of the method of the present invention, wherein the solution containing the second cellulose nanofiber is heated at the temperature in the range of 60° C. to 121° C., and preferably in the range of 60° C. to 80° C. in the step of (d).

In a preferred embodiment of the method of the present invention, wherein the lens body having first cellulose nanofiber layer is immersed in the solution containing the second cellulose nanofiber for a time in the range of 20 minutes to 90 minutes, and preferably in the range of 30 minutes to 60 minutes in the step of (d).

In a preferred embodiment of the method of the present invention, wherein the concentration of the second cellulose nanofiber is in the range of 500 ppm to 1500 ppm, and preferably in the range of 500 ppm to 1000 ppm.

The above and other aspects of the invention will become better understood with regard to the following detailed description of the preferred but non-limiting embodiment(s). These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be affected without departing from the spirit and scope of the novel concepts of the disclosure.

DETAILED DESCRIPTION OF THE INVENTION

In the following detailed description, for purposes of explanation, numerous specific details are set forth in order to provide a thorough understanding of the disclosed embodiments. It will be apparent, however, that one or more embodiments may be practiced without these specific details.

It is apparent that departures from specific designs and methods described and shown will suggest themselves to those skilled in the art and may be used without departing from the spirit and scope of the invention. The present invention is not restricted to the particular constructions described and illustrated, but should be construed to cohere with all modifications that may fall within the scope of the appended claims.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

The invention, in one aspect, provides an ophthalmic lens comprising a lens body, a polydopamine layer and a first cellulose nanofiber (CNF) layer.

In an embodiment of the present invention, the lens body is made of a silicone hydrogel. The silicone hydrogel can comprise but not limited to at least one siloxane macromer, at least one hydrophilic monomer and an initiator.

Suitable siloxane macromer can be the siloxane macromer suitably used in conventional ophthalmic lens materials, particularly the siloxane macromer suitably used in conventional contact lens materials.

Suitable hydrophilic monomer can be, such as N-vinylpyrrolidone (NVP), 2-hydroxyethyl methacrylate (HEMA), N,N'-dimethylacrylamide (DMA), methyl acrylic acid (MAA), N,N'-diethylacrylamide, N-isopropylamide, 2-hydroxypropyl acrylate, vinyl acetate, N-acrylolmorpholine, 2-dimethylaminoethyl acrylate or a combination thereof, but not limited thereto.

Suitable initiator can be the initiator suitably used in conventional ophthalmic lens materials, for example, thermal initiator or photo initiator. Suitable thermal initiator can be but not limited to, for example, 2,2'-azobis(2,4-dimethylvaleronitrile) (ADVN), 2,2'-azobis(isobutyronitrile) (AIBN), 2,2'-azobis(2,4-dimethylvaleronitrile), 2,2'-azobis(2-methyl-propanenitrile), 2,2'-azobis(2-methyl-butanenitrile) or benzoyl peroxide. Suitable photo initiator can be, but not limited to, for example, 2,4,6-trimethylbenzoyl diphenyl oxide, 2-hydroxy-2-methylpropiophenone, ethyl (2,4,6-trimethylbenzoly)phenylphosphinate or 2,2-diethoxyacetophenone.

The silicon hydrogel can further comprise a crosslinking agent selectively. Suitable crosslinking agent can be, for example, ethylene glycol dimethacrylate (EGDMA), trimethylolpropane trimethacrylate (TMPTA), triethylene ethylene glycol dimethacrylate (TEGDMA), tetraethylene ethylene glycol dimethacrylate (TrEGDMA), Poly(ethylene glycol) dimethacrylate, trimethylpropane trimethacrylate, vinyl methacrylate, ethylenediamine dimethyl acrylamide, glyceryl methacrylate, triallyisocyanurate, triallyl cyanurate or a combination thereof.

The silicone hydrogel can further include but not limited to crosslinking agent, dye, UV-blocking agent, solvent or a combination thereof as needed.

The ophthalmic lens of the present invention comprises a polydopamine layer formed on the surface of the lens body and the polydopamine layer is adhered on the surface of the lens body. Polydopamine has adhesion property due to the catechol functional group thereof and can form covalent bond or non-covalent bond, such as hydrogen bond, van der Waals' force or a combination of stacking force, to a surface of a base material. Moreover, the polydopamine layer provides hydrophilic hydroxy functional groups and amine functional groups to the surface of lens body of the present invention, the hydrophilicity and chemical versatility of the lens body can be enhanced. Not only the cellulose nanofiber can be adhered on the lens body by the adhesion property of the polydopamine, but also the hydrophobic surface of the ophthalmic lens can be improved by the hydrophilicity of the polydopamine.

Cellulose nanofiber (CNF) is made of wood-derived fiber and can be manufactured by micro-refining the pulp or fiber to the nano level. The width of cellulose nanofiber is about in the range of 1 nm to 20 nm and the length of cellulose nanofiber is about in the range of 100 nm to 300 nm. The method for micro-refining the pulp or fiber can be conducted by the conventional method, such as, grinding by a grinding machine, a high pressure homogenizer, a medium mixing mill, mortar, a grinding machine, a biaxial extruder, a bead mill or the like in water or aqueous medium to manufacture cellulose nanofiber; by using microorganism to manufacture cellulose nanofiber; adding pulp or fiber into fibrillated resin without water or asqueous medium and providing shear force mechanically to manufacture cellulose nanofiber; dissolving fiber into solvent and electrospinning therefrom to generate cellulose nanofiber; oxidizing the cellulose in the pulp with an oxidizing agent or using catalyst converter to separate and nanoize into cellulose nanofiber due to electrostatic repulsion.

The first cellulose nanofiber (CNF) layer is bonded to the polydopamine layer. In an embodiment of the present invention, the first cellulose nanofiber (CNF) layer is bonded to the polydopamine layer by a crosslinking agent. The cellulose nanofiber has great hydrophilicity, therefore the hydrophobic surface of the ophthalmic lens can be improved and result in good wearing comfortability.

Optionally, a hydrophilic layer formed from a second cellulose nanofiber can be bonded to the first cellulose nanofiber layer. In an embodiment of the present invention, the second cellulose nanofiber layer is bonded to the first cellulose nanofiber layer by the crosslinking agent of the first cellulose nanofiber layer to further improve the hydrophilicity of the ophthalmic lens.

In another embodiment of the present invention, the ophthalmic lens comprises a lens body, a polydopamine layer, a first cellulose nanofiber (CNF) layer and a functional layer. The functional layer, for example, can be bonded to the first cellulose nanofiber layer by the crosslinking agent of the first cellulose nanofiber layer.

The functional layer can be disposed as different needed. For example, the functional layer can be form from a second cellulose nanofiber to improve the hydrophilicity of the ophthalmic lens by the hydrophilicity of the cellulose nanofiber. The functional layer can be form from zwitterionic polymer or zwitterionic copolymer to improve the deposit resistance and antimicrobial properties of the ophthalmic lens. The functional layer can be form from reactive dye with reactive functional group to change the appearance of the ophthalmic lens. The functional layer can be the combination of the above mentioned material, but not limited thereto.

The first cellulose nanofiber is bonded to the polydopamine layer of the ophthalmic lens of the present invention by the crosslinking agent. Due to the great hydrophilicity of the cellulose nanofiber, the problem of hydrophobic surface of silicon hydrogel ophthalmic lens can be avoided. Moreover, polydopamine has excellent biocompatibility and hydrophilic function groups, thus not only the cellulose nanofiber can be adhered on the lens body, but also the wearing comfortability can be enhanced. Although the ophthalmic lens of the present invention comprises the polydopamine layer, the optical properties of the ophthalmic lens of the present invention can still be retained by using the crosslinking agent to reduce the usage amount of the polydopamine.

According to another aspect of the present invention, a method for manufacturing ophthalmic lens with excellent deposit resistance, high antimicrobial property, high hydrophilicity, desired optical properties and surface lubricity is provided. The present method can include but not limited to the following steps. The method for manufacturing ophthalmic lens has advantages of simple to produce and high effectively.

Firstly, a lens body is provided, which is made of a silicon hydrogel. And then, the lens body is immersed in a polydopamine solution for coating a polydopamine layer on the surface of the lens body.

The polydopamine solution can be prepared, for example, by polymerizing a dopamine in alkaline aqueous solution to form the polydopamine solution. In an embodiment of the method of the present invention, the polydopamine solution is prepared by dissolving a dopamine in an aqueous sodium bicarbonate solution. In an embodiment of the method of the present invention, the concentration of the polydopamine solution is in the range of 50 ppm to 400 ppm, and preferably in the range of 100 ppm to 300 ppm. When the concentration of the polydopamine solution is higher than above mentioned range, the optical properties of the lens will be affected. When the concentration of the polydopamine solution is lower than above mentioned range, the polydopamine layer is formed insufficiently on the surface of the lens body for cellulose nanofiber to be adhered thereon. In such a case, the hydrophilicity of the ophthalmic lens is decreased.

In a preferred embodiment of the method of the present invention, when the lens body is immersed in the polydopamine solution, the polydopamine solution is heated at the temperature in the range of 40° C. to 80° C., and preferably in the range of 40° C. to 60° C. for a period in the range of 5 minutes to 30 minutes, and preferably in the range of 10 minutes to 20 minutes. When the lens body is immersed in the polydopamine solution, the time for immersing the lens body in the polydopamine solution or the heating temperature is higher than above mentioned range, the surface of the lens body will be brownish and thus, the light transmittance and the optical properties of the lens will be reduced. When the lens body is immersed in the polydopamine solution, the time for immersing the lens body in the polydopamine solution or the heating temperature is lower than above mentioned range, the polydopamine layer is formed insufficiently on the surface of the lens body for the cellulose nanofiber to be bonded thereon. In such a case, the hydrophilicity of the ophthalmic lens might be decreased.

After the polydopamine layer is coated on the lens body, the polydopamine-coated lens body is washed. In an embodiment of the method of the present invention, the polydopamine-coated lens body is washed by pure water to remove the residual polydopamine. The lens body is washed for about 5 minutes, but the time can be adjusted as needed.

After washing, the washed polydopamine-coated lens body is immersed in a solution containing a first cellulose nanofiber and a crosslinking agent to form a first cellulose nanofiber layer bonded to the polydopamine layer.

In an embodiment of the method of the present invention, the concentration of the first cellulose nanofiber is in the range of 300 ppm to 1500 ppm, and preferably in the range of 500 ppm to 1000 ppm.

Suitable crosslinking agent can be, for example, 1,4-butanediol diglycidyl ether (BDDE), polyethylene glycol diacrylate (PEGDA), ethylene glycol diglycidyl ether, 1,6-hexanediol diglycidyl ether, polypropylene glycol diglycidyl ether, polytetramethylene glycol diglycidyl ether, neopentyl glycol diglycidyl ether, polyglycerol polyglycidyl ether, diglycerolpolyglycidyl ether, glycerol polyglycidyl ether, tri-methylolpropanepolyglycidyl ether, pentaerythritolpolyglycidyl ether, sorbitol polyglycidyl ether, 1,2,7,8-diepoxyoctane, 1,3-butadiene diepoxide, polyamidoamineepichlorohydrin, copolymer of dimethylamine and epichlorohydrin or a combination thereof, but not limited thereto. In an embodiment of the method of the present invention, the crosslinking agent can be 1,4-butanediol diglycidyl ether (BDDE). The concentration of the crosslinking agent is in the range of 100 ppm to 600 ppm, and preferably in the range of 200 ppm to 500 ppm.

In a preferred embodiment of the method of the present invention, when the polydopamine-coated lens body is immersed in the solution containing the first cellulose nanofiber and the crosslinking agent, the solution containing the first cellulose nanofiber and the crosslinking agent can be heated at the temperature in the range of 60° C. to 121° C., and preferably in the range of 60° C. to 80° C. The time for immersing the polydopamine-coated lens body in the solution containing the first cellulose nanofiber and the crosslinking agent is in the range of 20 minutes to 90 minutes, and preferably in the range of 30 minutes to 60 minutes. As the heating temperature is higher than the above mentioned range and/or the time for immersing the polydopamine-coated lens body therein is longer than the above mentioned range, the optical property of the ophthalmic lens will be affected. As the heating temperature is lower than the above mentioned range and/or the time for immersing the polydopamine-coated lens body therein is shorter than the above mentioned range, the hydrophilicity of the ophthalmic lens will be affected.

Optionally, after forming the first cellulose nanofiber layer, the lens body having first cellulose nanofiber layer can be immersed in a solution containing second cellulose nanofiber to form a second cellulose nanofiber layer bonded on the first cellulose nanofiber layer by the crosslinking agent.

In a preferred embodiment of the method of the present invention, the concentration of the second cellulose nanofiber is in the range of 500 ppm to 1500 ppm, and preferably in the range of 500 ppm to 1000 ppm. And the time for immersing the lens body having first cellulose nanofiber layer in the solution containing the second cellulose nanofiber is in the range of 20 minutes to 90 minutes, and preferably in the range of 30 minutes to 60 minutes. Optionally, when the lens body having first cellulose nanofiber layer is immersed in the solution containing the second cellulose nanofiber, the solution containing the second cellulose nanofiber can be heated at the temperature in the range of 60° C. to 121° C., and preferably in the range of 60° C. to 80° C.

The second cellulose nanofiber is bonded to the first cellulose nanofiber layer by the crosslinking agent. The surface hydrophilicity of the ophthalmic lens of the present invention can be further improved by the hydrophilicity of the second cellulose nanofiber.

In further another embodiment of the method of the present invention, optionally, after forming the first cellulose nanofiber layer, the lens body having first cellulose nanofiber layer can be immersed in a solution containing functional material to form a functional layer bonded to the first cellulose nanofiber layer by the crosslinking agent. The functional layer can be, for example, hydrophilic layer, antimicrobial layer, colored layer or the combination thereof. The functional material can be but not limited to second cellulose nanofiber for improving the surface hydrophilicity of the ophthalmic lens, zwitterionic polymer or zwitterionic copolymer for improving the antimicrobial property of the ophthalmic lens, reactive dye for changing the appearance of the ophthalmic lens or a combination thereof.

After immersing the polydopamine-coated lens body in the solution containing the first cellulose nanofiber and the crosslinking agent to form a first cellulose nanofiber layer bonded to the polydopamine layer, a sterilization treatment can be conducted selectively to the lens body. The sterilization treatment suitably used in conventional method for manufacturing ophthalmic lens can be used in the method of the present invention.

In an embodiment of the method of the present invention, after taking out the lens body from the solution containing the first cellulose nanofiber and the crosslinking agent, the lens body is then immersed in a phosphate buffer solution to conduct a sterilization treatment and packing process. In another embodiment of the method of the present invention, the solution containing the first cellulose nanofiber and the crosslinking agent is prepared with a phosphate buffer solution, after immersing the lens body in the phosphate buffer solution containing the first cellulose nanofiber and the crosslinking agent, a sterilization treatment and packing process are conducted directly.

Accordingly, the method for manufacturing ophthalmic lens of the present invention can be introduced into conventional method for manufacturing contact lens, the first cellulose nanofiber layer can bond to the polydopamine layer of the surface of the ophthalmic lens during lens sterilization treatment and packing process to simplify the surface modification of the lens therefore.

In comparison to the conventional surface modified process for medical equipment, the method of the present invention comprises the steps of immersing the lens body in the polydopamine solution, washing the polydopamine-coated lens body, and then, immersing the polydopamine-coated lens body in the solution containing the cellulose nanofiber and the crosslinking agent. The ophthalmic lens manufactured by the method of the present invention comprises cellulose nanofiber layer, thus, the ophthalmic lens manufactured by the method of the present invention has high hydrophilicity and desired optical properties can still be retained by reducing the concentration of the polydopamine solution used in the manufacturing process.

The present invention will be explained in further detail with reference to the examples. However, the present invention is not limited to these examples.

Preparation Example 1: The Preparation of Polydopamine Solution 1 g of dopamine was dissolved in 1000 ml of aqueous sodium bicarbonate solution (pH is 8.5) and stirred for 24 hours to form a polydopamine solution with a concentration of 1000 ppm. And then the polydopamine solution was diluted with aqueous sodium bicarbonate solution (pH is 8.5) to 100 ppm to obtain a resulting polydopamine solution.

Preparation Example 2: The Preparation of Silicon Hydrogel Lens Body 4.44 g of isophorone diisocyanate, 0.0025 g of dibutyltin dilaurate as catalysts and 40 mL of methylene chloride were added into a flask to form a solution, and the solution was stirred under a stream of nitrogen. Then, 20 g of α-butyl-ω-[3-(2,2-(hydroxymethyl) butoxy) propyl] polydimethylsiloxane was accurately weighed and added dropwise to the solution over about 1 hour. After the solution reacting at room temperature for 12 hours, the resulting reaction product was washed with a large amount of water, and then dehydrated and filtered to obtain a raw product. Then, the methylene chloride was evaporated to obtain a first siloxane macromer.

8.88 g of isophorone diisocyanate, 0.0025 g of dibutyltin dilaurate as catalysts and 40 mL of methylene chloride were added into a flask to form a solution, and the solution was stirred under a stream of nitrogen. Then, 20 g of polydimethylsiloxane was accurately weighed and added dropwise to the solution over about 1 hour. After the solution reacting at room temperature for 12 hours, another 0.0025 g of dibutyltin dilaurate and 14.4 g of polyethylene glycol monomethacrylate were accurately weighed and added dropwise to the solution over about 1 hour. After the solution reacting at room temperature for another 12 hours, the resulting reaction product was washed with a large amount of water, and then dehydrated and filtered to obtain a raw product. Then, the methylene chloride was evaporated to obtain a second siloxane macromer.

41.8 g of the first siloxane macromer, 6.3 g of the second siloxane macromer, 0.7 g of azobisisoheptonitrile (ADVN), 46.96 g of N-vinylpyrrodine (NVP), 6.3 g of 2-hydroxyethyl methacrylate (HEMA), 1 g of ethylene glycol dimethylacrylate (EGDMA) and 25.1 g of hexanol were mixed and stirred about 1 hour to form a mixture. Then, the mixture was injected into a mold of contact lens made of polypropylene (PP) and heated to initiate the radical polymerization thereof at 60° C. for 1 hour, 80° C. for 2 hours and 135° C. for 2 hours. After the polymerization was completed, the mold was immersed in 80% alcohol solution for 1 hour and the resulting molded lens was taken out of the mold to obtain a silicon hydrogel lens body.

Preparation Example 3: The Preparation of Cellulose Nanofiber Solution 0.1 g of cellulose nanofiber (available from Sugino, Japan) and 0.05 g of 1,4-butanediol diglycidyl ether (BDDE) was dissolved in 99.85 g of deionized water and stirred for 15 minutes to obtain a solution containing cellulose nanofiber and crosslinking agent, wherein the concentration of the cellulose nanofiber was 1000 ppm and the concentration of 1,4-butanediol diglycidyl ether as crosslinking agent was 500 ppm.

Preparation Example 4: The Preparation of Cellulose Nanofiber Solution 0.1 g of cellulose nanofiber (available from Sugino, Japan) and 0.05 g of polyethylene glycol diacrylate (PEGDA) was dissolved in 99.85 g of deionized water and stirred for 15 minutes to obtain a solution containing cellulose nanofiber and crosslinking agent, wherein a concentration of the cellulose nanofiber was 1000 ppm and a concentration of polyethylene glycol diacrylate (PEGDA) as crosslinking agent was 500 ppm.

EXAMPLE 1

First, the silicon hydrogel lens body of preparation example 2 was immersed in the polydopamine solution of preparation example 1 at 50° C. for 15 minutes and washed by water.

And then the silicon hydrogel lens body was immersed in the aqueous solution containing 1000 ppm cellulose nanofiber and 500 ppm 1,4-butanediol diglycidyl ether at 80° C. for 60 minutes and washed by water to obtain the ophthalmic lens. The results of optical property, physical property, and antimicrobial tests of the ophthalmic lens were shown as the following Table 1.

EXAMPLE 2

First, the silicon hydrogel lens body of preparation example 2 was immersed in the polydopamine solution of preparation example 1 at 50° C. for 15 minutes and washed by water.

And then the silicon hydrogel lens body was immersed in the aqueous solution containing 1000 ppm cellulose nanofiber and 500 ppm polyethylene glycol diacrylate (PEGDA) at 80° C. for 60 minutes and washed by water to obtain the ophthalmic lens. The results of optical property, physical property, and antimicrobial tests of the ophthalmic lens were shown as the following Table 1.

EXAMPLE 3

First, the silicon hydrogel lens body of preparation example 2 was immersed in the polydopamine solution of preparation example 1 at 50° C. for 15 minutes and washed by water.

And then the silicon hydrogel lens body was immersed in the aqueous solution containing 1000 ppm cellulose nanofiber and 500 ppm 1,4-butanediol diglycidyl ether (BDDE) at 80° C. for 60 minutes, then the lens body was taken out from the solution. Next, the lens body was immersed in an aqueous solution containing 1000 ppm cellulose nanofiber at 80° C. for 60 minutes. Finally, the lens body was washed by water to obtain the ophthalmic lens. The results of optical property, physical property, and antimicrobial tests of the ophthalmic lens were shown as the following Table 1.

EXAMPLE 4

First, the silicon hydrogel lens body of preparation example 2 was immersed in the polydopamine solution of preparation example 1 at 50° C. for 15 minutes and washed by water.

And then the silicon hydrogel lens body was immersed in the aqueous solution containing 1000 ppm cellulose nanofiber and 500 ppm polyethylene glycol diacrylate (PEGDA) at 80° C. for 60 minutes, then the lens body was taken out from the solution. Next, the lens body was immersed in an aqueous solution containing 1000 ppm cellulose nanofiber at 80° C. for 60 minutes. Finally, the lens body was washed by water to obtain the ophthalmic lens. The results of optical property, physical property, and antimicrobial tests of the ophthalmic lens were shown as the following Table 1.

Comparative Example 1

The Comparative Example 1 was the silicone hydrogel lens body of Preparation Example 2, and the surface of the lens body did not comprise the polydopamine layer and the cellulose nanofiber layer. The results of optical property, physical property, and antimicrobial tests of the ophthalmic lens were shown as the following Table 1.

Comparative Example 2

The silicon hydrogel lens body of preparation example 2 was immersed in a polydopamine solution having a concentration of 1000 ppm at 80° C. for 30 minutes and washed by water.

Measurement of the Visible Light Transmittance of Ophthalmic Lens

The transmittance of visible light with wavelength of 370 nm-780 nm of the ophthalmic lens was measured by UV-Visible Spectrophotometer (V-650, commercially available from JASCO, Japan).

Measurement of Contact Angle

The ophthalmic lens was immersed in water for 1 hour. Then, the ophthalmic lens was removed therefrom and was taken to remove all surface water by wet wipe. After that, the contact angle of ophthalmic lens was measured by Contact Angle Wafer Surface Analysis Inspection Goniometer (VCA2500XE, commercially available from AST Products, USA).

The Appearance Test

The appearance of the ophthalmic lens is observed by eyes. In the standard list, 1 represents that large area of the ophthalmic lens is dirty, 2 represents that half of the ophthalmic lens is dirty, 3 represents one third of the ophthalmic lens is dirty, 4 represents small area of the ophthalmic lens is dirty or dotted dirty, 5 represents the ophthalmic lens is clean.

Table 1: The measurement results of Examples and Comparative Examples

From the results shown in Table 1, the contact angles of Example 1 to Example 4 all are 10°. Therefore, Examples 1 to Example 4 of the present invention have more excellent hydrophilicities than Comparative Example 1. In addition, the visible light transmittances of ophthalmic lenses of Example 1 to Example 4 are 92%, it can be seen that the desirable optical and physical properties of ophthalmic lens can still be retained. The visible light transmittance of ophthalmic lens of Comparative Example 1 is too low to be using as an ophthalmic lens.

While the invention has been described by way of example(s) and in terms of the embodiments, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An ophthalmic lens, comprising:
   a lens body;
   a polydopamine layer formed on a surface of the lens body by immersing the lens body in a polydopamine solution prepared from dopamine in alkaline environments and heating at the temperature in the range of 40° C. to 80° C. for a period of time in the range of 5 minutes to 30 minutes; and
   a first cellulose nanofiber (CNF) layer bonded to the polydopamine layer.

2. The ophthalmic lens according to claim 1, wherein the lens body is made of a hydrogel or a silicon hydrogel.

3. The ophthalmic lens according to claim 1, further comprising a hydrophilic layer formed by bonding a second cellulose nanofiber to the first cellulose nanofiber (CNF) layer.

4. An ophthalmic lens, comprising:
   a lens body;
   a polydopamine layer formed on a surface of the lens body by immersing the lens body in a polydopamine solution prepared from dopamine in alkaline environments and heating at the temperature in the range of 40° C. to 80° C. for a period of time in the range of 5 minutes to 30 minutes;
   a first cellulose nanofiber (CNF) layer bonded to the polydopamine layer; and
   a functional layer bonded to the first cellulose nanofiber layer.

5. The ophthalmic lens according to claim 4, wherein the functional layer is selected from one of the group consisting of a second cellulose nanofiber, a zwitterionic polymer, a zwitterionic copolymer and a reactive dye or a combination thereof.

6. A method for manufacturing an ophthalmic lens, comprising steps of:

|  | Example | | | | Comparative Example | |
| --- | --- | --- | --- | --- | --- | --- |
|  | 1 | 2 | 3 | 4 | 1 | 2 |
| Visible light transmittance (%) | 92 | 92 | 92 | 92 | 98 | 65.5 |
| Contact angle (°) | 10 | 10 | 10 | 10 | 94.6 | 50.3 |
| Appearance | 3.5 | 4.5 | 3.5 | 4.5 | 5 | 1 |

(a) providing a lens body, and immersing the lens body in a polydopamine solution prepared from dopamine in alkaline environments and heating at the temperature in the range of 40° C. to 80° C. for a period of time in the range of 5 minutes to 30 minutes to coat a polydopamine layer on a surface of the lens body;

(b) washing the polydopamine-coated lens body; and (c) immersing the polydopamine-coated lens body in a solution containing a first cellulose nanofiber and a crosslinking agent to form a first cellulose nanofiber layer bonded to the polydopamine layer.

7. The method for manufacturing the ophthalmic lens according to claim 6, wherein the concentration of the polydopamine solution is in the range of 50 ppm to 400 ppm.

8. The method for manufacturing the ophthalmic lens according to claim 6, wherein the solution containing the first cellulose nanofiberand and the crosslinking agent is heated at the temperature in the range of 60° C. to 121° C. in the step of (c).

9. The method for manufacturing the ophthalmic lens according to claim 6, wherein the polydopamine-coated lens body is immersed in the solution containing the first cellulose nanofiberand and the crosslinking agent for a time in the range of 20 minutes to 90 minutes in the step of (c).

10. The method for manufacturing the ophthalmic lens according to claim 6, wherein the concentration of the first cellulose nanofiber is in the range of 300 ppm to 1500 ppm.

11. The method for manufacturing the ophthalmic lens according to claim 6, wherein the crosslinking agent is selected from one of the group consisting of 1,4-butanediol diglycidyl ether (BDDE), polyethylene glycol diacrylate (PEGDA), ethylene glycol diglycidyl ether, 1,6-hexanediol diglycidyl ether, polypropylene glycol diglycidyl ether, polytetramethylene glycol diglycidyl ether, neopentyl glycol diglycidyl ether, polyglycerol polyglycidyl ether, diglycerolpolyglycidyl ether, glycerol polyglycidyl ether, tri-methylolpropanepolyglycidyl ether, pentaerythritolpolyglycidyl ether, sorbitol polyglycidyl ether, 1,2,7,8-diepoxyoctane, 1,3-butadiene diepoxide, polyamidoamineepichlorohydrin and copolymer of dimethylamine and epichlorohydrin or a combination thereof.

12. The method for manufacturing the ophthalmic lens according to claim 6, wherein the concentration of the crosslinking agent is in the range of 100 ppm to 600 ppm.

13. The method for manufacturing the ophthalmic lens according to claim 6, further comprising the step of (d) immersing the lens body having first cellulose nanofiber layer in a solution containing a second cellulose nanofiber to form a second cellulose nanofiber layer on the first cellulose nanofiber layer.

14. The method for manufacturing the ophthalmic lens according to claim 13, wherein the solution containing the second cellulose nanofiber is heated at the temperature in the range of 60° C. to 121° C. in the step of (d).

15. The method for manufacturing the ophthalmic lens according to claim 13, wherein the lens body having first cellulose nanofiber layer is immersed in the solution containing the second cellulose nanofiber for a time in the range of 20 minutes to 90 minutes in the step of (d).

16. The method for manufacturing the ophthalmic lens according to claim 13, wherein the concentration of the second cellulose nanofiber is in the range of 500 ppm to 1500 ppm.

* * * * *